(12) United States Patent
Towler et al.

(10) Patent No.: US 6,832,995 B1
(45) Date of Patent: Dec. 21, 2004

(54) CAUTERIZING SCALPEL

(75) Inventors: Gavin P. Towler, Barrington, IL (US);
Anil R. Oroskar, Oakbrook, IL (US);
Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 164 days.

(21) Appl. No.: 10/253,866

(22) Filed: Sep. 24, 2002

Related U.S. Application Data (63) Continuation-in-part of application No. 10/200,794, filed on Jul. 22, 2002.

(51) Int. Cl.⁷ .............................................. A61B 18/06
(52) U.S. Cl. ........................................ 606/27; 606/28
(58) Field of Search ..................................... 606/27, 28

(56) References Cited

U.S. PATENT DOCUMENTS

| | | | |
|---|---|---|---|
| 4,290,435 A | 9/1981 | Waggott | 128/800 |
| 4,627,435 A | 12/1986 | Hoskin | 128/303.1 |
| 4,679,561 A | 7/1987 | Doss | 128/422 |
| 4,737,628 A | 4/1988 | Lovoi | 250/226 |
| 4,796,622 A * | 1/1989 | Lu et al. | 606/28 |
| 4,872,458 A | 10/1989 | Kanehira et al. | 128/401 |
| 5,186,181 A | 2/1993 | Franconi et al. | 128/804 |
| 5,251,645 A | 10/1993 | Fenn | 607/154 |
| 5,324,299 A | 6/1994 | Davison et al. | 606/167 |
| 5,342,358 A * | 8/1994 | Daikuzono | 606/45 |
| 5,354,258 A | 10/1994 | Dory | 601/3 |
| 5,366,456 A | 11/1994 | Rink et al. | 606/16 |
| 5,528,561 A | 6/1996 | Castanis | 368/93 |
| 5,571,098 A | 11/1996 | Domankevitz et al. | 606/15 |
| 5,707,401 A | 1/1998 | Talmore | 607/88 |
| 5,776,175 A | 7/1998 | Eckhouse et al. | 607/100 |
| 6,051,005 A | 4/2000 | Brandsey et al. | 606/148 |
| 6,132,428 A | 10/2000 | VanDusseldorp | 606/46 |
| 6,159,200 A | 12/2000 | Verdura et al. | 606/1 |
| 6,165,184 A | 12/2000 | Verdura et al. | 606/148 |
| 6,235,037 B1 | 5/2001 | East et al. | 606/119 |
| 6,275,738 B1 | 8/2001 | Kasevich et al. | 607/101 |
| 6,312,435 B1 | 11/2001 | Wallace et al. | 606/130 |
| 6,337,998 B1 | 1/2002 | Behl et al. | 607/101 |
| 6,379,347 B1 | 4/2002 | Maki et al. | 606/17 |
| 6,383,179 B1 | 5/2002 | Neuberger | 606/16 |
| 6,394,998 B1 | 5/2002 | Wallace et al. | 606/1 |
| 6,416,524 B1 | 7/2002 | Critz et al. | 606/167 |
| 6,419,684 B1 | 7/2002 | Heisler et al. | 606/170 |

* cited by examiner

Primary Examiner—Roy D. Gibson
Assistant Examiner—Henry M Johnson, III
(74) Attorney, Agent, or Firm—John G. Tolomei; Frank S. Molinaro; Arthur E. Gooding (57) ABSTRACT

A device is disclosed for simultaneous cutting and cauterizing of tissue. The device comprises a cutting edge of a blade. The blade defines a channel within the blade wherein the outlet end of the channel is near the cutting edge. A catalyst is disposed near the outlet end. The channel carries a gaseous mixture to the catalyst where the mixture reacts in the presence of the catalyst and generated heat. The heat generated cauterizes blood vessels as the blade cuts through tissue.

52 Claims, 7 Drawing Sheets

CAUTERIZING SCALPEL

CROSS-REFERENCE TO RELATED APPLICATIONS

This application is a continuation-in-part of co-pending U.S. application Ser. No. 10/200,794, filed Jul. 22, 2002, all of which is incorporated by reference.

FIELD OF THE INVENTION

The present invention relates to surgical cutting instruments. In particular, this invention relates to scalpels that incorporate means for cauterizing blood vessels during usage of the scalpel.

BACKGROUND OF THE INVENTION

Surgical operations often involve the cutting of a patient's tissue. Usually, the tissue is cut with a scalpel, a sharp edged cutting instrument. However, the cutting of a patient's tissue is also usually accompanied by an undesired flow of blood from small blood vessels within the tissue. Reducing, or eliminating this blood flow is advantageous to the patient by reducing blood loss and to the surgeon by removing or reducing an obstruction to the surgeon's view of the incised tissue.

Scalpels making use of lasers for heat sources can be used to heat and irradiate the incised tissue. Light of an appropriate wavelength is absorbed by the tissue, and the optical energy is converted to thermal energy to cauterize the tissue. Cutting instruments of this type are described in U.S. Pat. Nos. 6,383,179; 5,571,098; 5,366,456; and 4,627,435. These devices can use the laser to incise the tissue as well as cauterize, or use an optically transparent material for the cutting instrument coupled with a bundle of optical fibers for directing the laser to the area of interest.

Another method of providing cauterizing heat with a scalpel is the use of ultrasonics. U.S. Pat. No. 5,324,299 describes such a device wherein the scalpel blade is vibrated at a rate around 55,000 cycles per second. The vibration generates ultrasound waves for heating the tissue, however, there is only limited cauterizing ability.

Control of blood loss can be achieved by cauterizing the small blood vessels in the tissue at the time the tissue is cut. Cauterization of the blood vessels is achieved by applying heat at the vessels. It is advantageous to apply the heat at the time the tissue is cut and at the tissue without exposing the tissue to radiation.

SUMMARY OF THE INVENTION

The present invention provides a device for cauterizing tissue during the process of cutting the tissue. The apparatus comprises a blade having a cutting edge. The blade has at least one channel formed within the blade, with each channel having an inlet end and an outlet end. The outlet end of each channel is positioned proximate to the cutting edge of the blade. The apparatus further includes a catalyst disposed proximate to the outlet end of each channel.

In one embodiment, the invention is a blade having a cutting edge. The blade has a main channel and a plurality of branch channels formed within the blade, with each branch channel having an inlet end and an outlet end and the main channel having an inlet end and at least one outlet end. The outlet end of each branch channel is positioned proximate to the cutting edge of the blade. The inlet end of each branch channel is in fluid communication with an outlet end of the main channel. The apparatus includes a catalyst disposed proximate to the outlet end of each branch channel.

In another embodiment, the invention further includes a mixer for mixing reactant gases to form a mixture and delivering the mixture to the inlet end of the channels. The mixer provides for a well-mixed gas composition to provide a substantially complete reaction of the reactant gases.

Other objects, advantages and applications of the present invention will become apparent to those skilled in the art from the following detailed description.

BRIEF DESCRIPTION OF THE DRAWINGS

The description herein makes reference to the accompanying drawings wherein like reference numerals refer to like parts throughout the several views and wherein.

DETAILED DESCRIPTION OF THE INVENTION

Surgical procedures usually require the cutting of a patient's tissue. However, accompanied with the tissue cutting is the flow of blood from the network of small capillaries in the tissue. The blood obstructs the surgeon's view, and the open capillaries present sites for possible entry of infection, as well as requiring blood replacement if the bleeding is extensive. Cauterizing the capillaries that have been cut will reduce the amount of blood flowing into the region of the cut, and will reduce the risk of infection by closing the ends of the capillaries. Cauterizing seals by applying heat to the site and by applying heat during the cutting process, the capillaries are closed as they are cut. The present invention is a scalpel blade that provides heat for cauterizing capillaries that have been cut.

Figures 1, 1A:
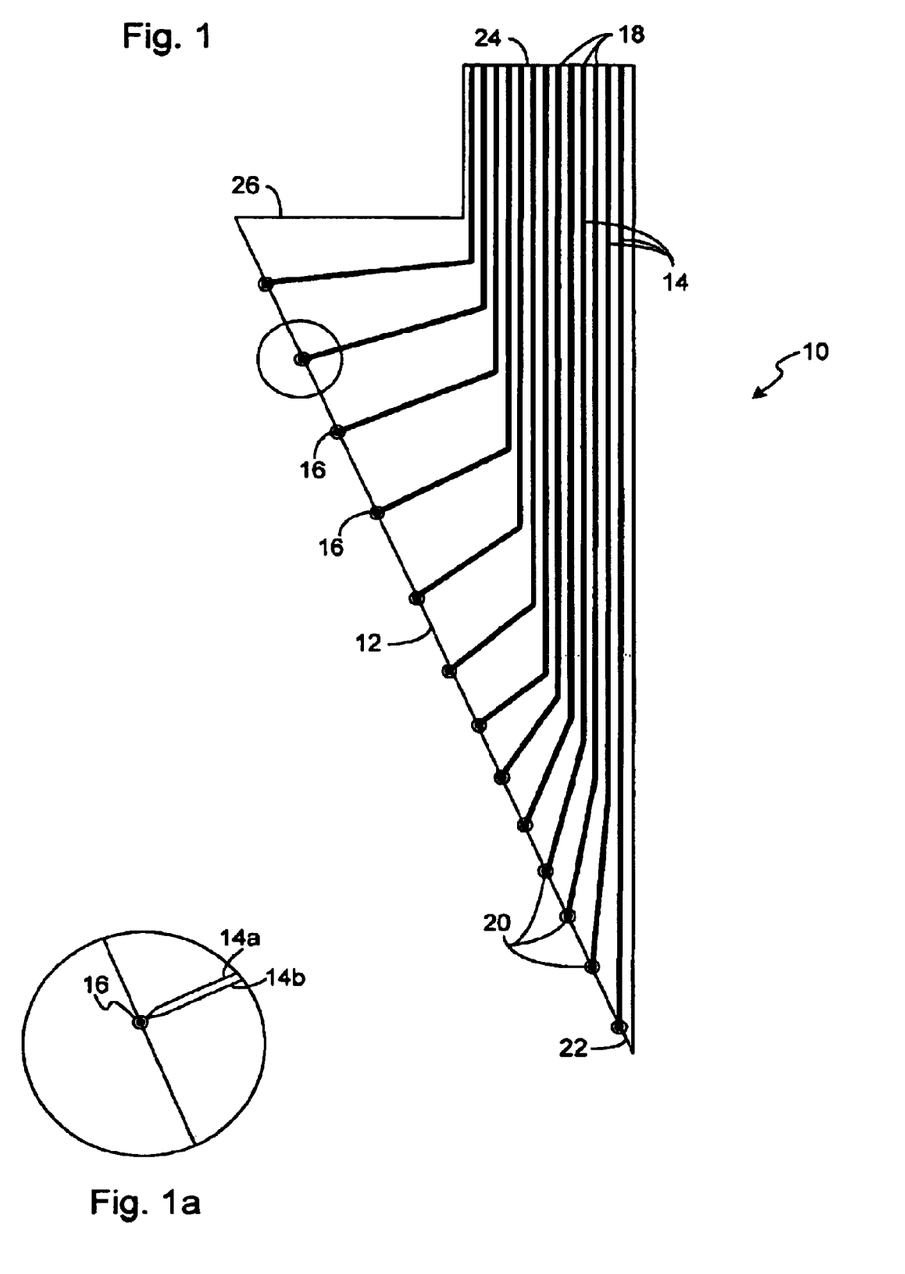
FIG. 1 is an embodiment of the cutting blade of the present invention.
FIG. 1a is an enlargement of one embodiment of a primary channel.

The present invention, as shown in FIG. 1, is an apparatus for cutting that includes a blade 10 having a cutting edge 12. The blade 10 is formed with a plurality of primary channels 14 within the blade for the transport of chemical reactants to a catalyst 16. A mixture of chemical reactants is supplied to the inlet ends 18 of the channels 14. The mixture is carried to the cutting edge 12 of the blade 10 and flows over the catalyst 16. The catalyst 16 initiates an exothermic reaction, and the blade 10 heats up, supplying heat to cauterize capillaries as they are cut. The primary channels 14 have an inlet end 18 and an outlet end 20, with the catalyst 16 deposited near the outlet end 20. The blade 10 also has a distal edge 24 opposite the cutting edge 12. At least one of the inlet ends 18 of the primary channels 14 is situated near the distal edge 24 of the blade 10. The distal edge 24 provides a means to connect the blade 10 to a source of the mixture of chemical reactants. In an alternative, each primary channel 14 is comprised of a pair of secondary channels 14a, as shown in FIG. 1a. In this configuration one of the secondary channels 14a carries a first reactant and the other of the secondary channels 14a carries a second reactant. Each of the secondary channels 14a has an outlet that is proximate to the catalyst 16.

The channels 14 are formed as part of the design of the blade 10. The blade 10 is formed from two plates 26, 28 of material which are joined together. Prior to joining the two plates 26, 28, at least one of the plates 26, 28 has the groves cut into the plate 26. Upon joining the plates 26, 28, the channels 14 are formed. The grooves are cut into the plate 26 using any well known method for producing small grooves. Possible methods include for example chemical etching methods and other well-known methods for micro machining. The channels 14 have a diameter of less than about 400 micrometers. The diameter of the channels 14 must be sufficiently small such that the mixture flowing in the channels 14 is stable with respect to combustion and ignition. For medical purposes, a preferred mixture is hydrogen and oxygen. A preferred diameter of the channels 14 for a mixture of hydrogen and oxygen is less than about 100 micrometers.

The channels 14 are formed in a pattern to provide a distribution of the outlet ends 20 of the channels along the cutting edge 12 of the blade 10. One such pattern, as shown in FIG. 1, is a fanned array of channels such that the outlet ends 20 are uniformly distributed along the cutting edge 12. Although a uniform pattern is presented, any distribution of the channels 14 that position the outlet ends 20 in proximity to the cutting edge 12 is contemplated by this invention. Positioning the outlet ends 20 proximate to the cutting edge 12 enables heating of the blade in the region close to the cut tissue. The channels 14 can be distributed in any pattern deemed necessary to provide the appropriate heating of the blade 10. The channels 14 are preferably designed such that the pressure drop in each of the channels is substantially the same, providing uniform distribution of the mixture of reactants to the channel outlet ends 20. The uniform distribution of the mixture to the outlet ends 20, and in turn to the catalyst 16, provides for a substantially uniform heating of the cutting edge 12.

Alternately, a non-uniform distribution of the channel outlet ends 20 may be used to provide a greater supply of the mixture of reactants to a particular location on the blade 10. For example, if heating the region near the tip 22 of the blade 10 is desired, a greater concentration of channel outlet ends 20 would be positioned near the tip 22. An option to provide for non-uniform distribution of heating of the blade 10 is alternatively provided by non-uniform channel sizing. Channel diameters may be differentially sized to provide different flows of the reactant mixture through the channels 14.

Figure 2:
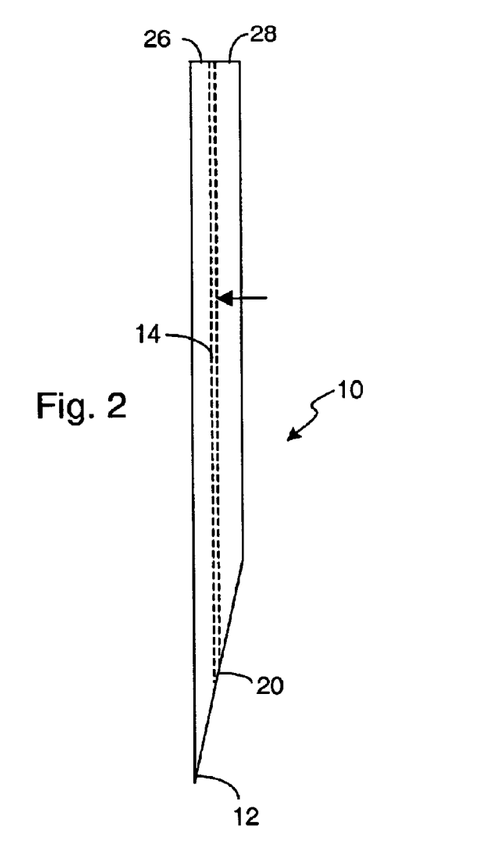
FIG. 2 is an edge view of a blade of the present invention.

Following formation of the channels 14 in the plate 26, the second plate 28 is placed in contact with the first plate 26 thereby covering the channels 14. An edge view of the blade 10 is shown in FIG. 2, and depicts a channel within the blade 10. The plates 26, 28 are joined together with any method to form a permanently bonded structure, such as diffusion bonding. The blade 10 is machined with any suitable method to produce the cutting edge 12. The channels 14 are sealed except for the inlet ends 18 and the outlet ends 20. FIG. 2 is an edge view of the blade 10 of the present invention, wherein a channel 14 is shown by dashed lines to lie within the blade 10 formed from two plates 26, 28. Machining the cutting edge 12 leaves the channel outlet ends 20 just behind the cutting edge 12. The distance behind the cutting edge can be adjusted, for example, by modifying the angle of the cutting edge 12, or by using plates 26, 28 of different relative thicknesses.

The blade 10 is made of any material having a sufficient hardness and capable of holding a sharp edge and formed with channels within the blade. The material is selected from the group consisting of stainless steels, ceramics such as silicon nitride, glasses, quartz, thermoset plastics, and alloys of metals such as incolloy, inconel, hastalloy, brasses, and bronzes. The choice of material is only limited by the permeability of the reactants, and whether or not the materials react substantially with the reactants. Preferably, the blade is made from a stainless steel.

The blade 10 can be treated to harden the surface. Conventional methods for blade hardening include, for example, the application of coatings or heat treatments, and are well known in the art of hardening a blade. Hardening and annealing processes are described in U.S. Pat. Nos. 6,330,750; 5,433,801 and 4,180,420 and are incorporated by reference in their entireties. Optionally, the bonding of the plates 26, 28 and the hardening of the blade 10 can be combined into a single process.

The blade 10 surface is also treated for the application of a catalyst. Methods for applying coatings are well known in the art, for example, the application of zirconium nitride is described in U.S. Pat. No. 6,330,750. The carbon microstructure can also be adjusted, as described in U.S. Pat. No. 4,180,420. The catalyst may be added to the blade 10 prior to hardening the blade, or may be added to the blade after treatment for hardening the blade. An example of catalyst addition to the blade after hardening, is electroplating the edge of the blade with an appropriate catalyst such as platinum.

The choice of catalysts is dependent on the choice of chemicals reacted at the blade. For non-medical applications, reactants for generating heat, include acetylene, methane, and other hydrocarbon gases that react with an oxidizing agent. Examples of oxidizing agents include air and oxygen. In the description which follows, hydrogen and oxygen will be used as examples of reactants, but it is understood that the invention is not limited to those reactants. Suitable catalysts for hydrogen combustion are well known and include the noble metals. Other catalyst materials include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, gallium, germanium, indium, thallium, tin, lead, antimony, bismuth, polonium, and mixtures thereof. Catalyst materials also include oxides of metals, and other oxides. Preferably, the catalyst is selected from platinum, palladium, rhenium, rhodium, nickel, iron, and mixtures thereof.

The blade 10 is affixed to a handle is such a manner to align the channel inlet ends 18 with corresponding channels in the handle. The inlet ends 18 of the channels are in fluid communication with a source of hydrogen-oxygen mixture. Preferably, the hydrogen-oxygen mixture is provided in the appropriate stoichiometric ratio for the combustion of hydrogen and oxygen to form water, i.e., a 2:1 molar or volume ratio of hydrogen to oxygen. The hydrogen and oxygen, or other reactants can be supplied by independent sources such as cylinders of gas. Preferably, the hydrogen and oxygen are produced by an electrolyzer. The electrolyzer separates water into the constituents of hydrogen and oxygen in the desired ratio. The hydrogen and oxygen are directed from individual conduits to a mixer. The reactants are well mixed in the mixer and flow to the channel inlet ends 18. Optionally, the reactants are fed to the channel inlet ends 18 and allowed to mix by diffusion while flowing along the channels 14 to the catalyst 16. One embodiment of the mixer is described in U.S. patent application Ser. No. 09/850,470, filed on May 7, 2001, which is incorporated by reference in its entirety.

Preferably, the electrolyzer is sized to dissociate water at a rate between about 0.01 milligrams/minute and about 10 grams/minute. The volume of gases to be reacted is easily controlled by the amount of electrical power supplied to the electrolyzer. Details of an electrolyzer are well known in the art, as demonstrated in U.S. Pat. No. 6,036,827, which is incorporated by reference. Optionally, a control system is incorporated in the electrolyzer to provide an upper limit on the amount of electrical power used by the electrolyzer, including, but not limited to, a fuse for shutting off power to the electrolyzer.

Figure 3:
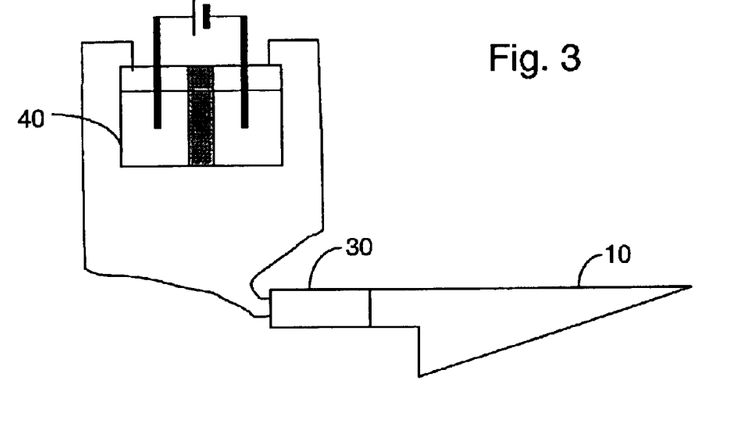
FIG. 3 is a diagram of the apparatus including an electrolyzer.

In one embodiment, as shown in FIG. 3, the mixer (not shown) is disposed within the handle 30. An electrolyzer 40 generates the hydrogen and oxygen to be reacted. The hydrogen is generated at one electrode and collected in a hydrogen reservoir. The hydrogen flows from the hydrogen reservoir through a hydrogen supply conduit to at least one hydrogen inlet to the mixer. The oxygen is generated at a second electrode and collected in an oxygen reservoir. The oxygen flows from the oxygen reservoir through an oxygen supply conduit to at least one oxygen inlet to the mixer. The hydrogen and oxygen are mixed within the mixer in a mixing chamber and flow out a mixing chamber outlet to the channel inlet ends 18 of the channels within the blade 10. Although a handle 30 is depicted in this embodiment, any appropriate blade holder is intended to be covered by this invention, including for example a clamp for manipulating the blade.

Figure 4:
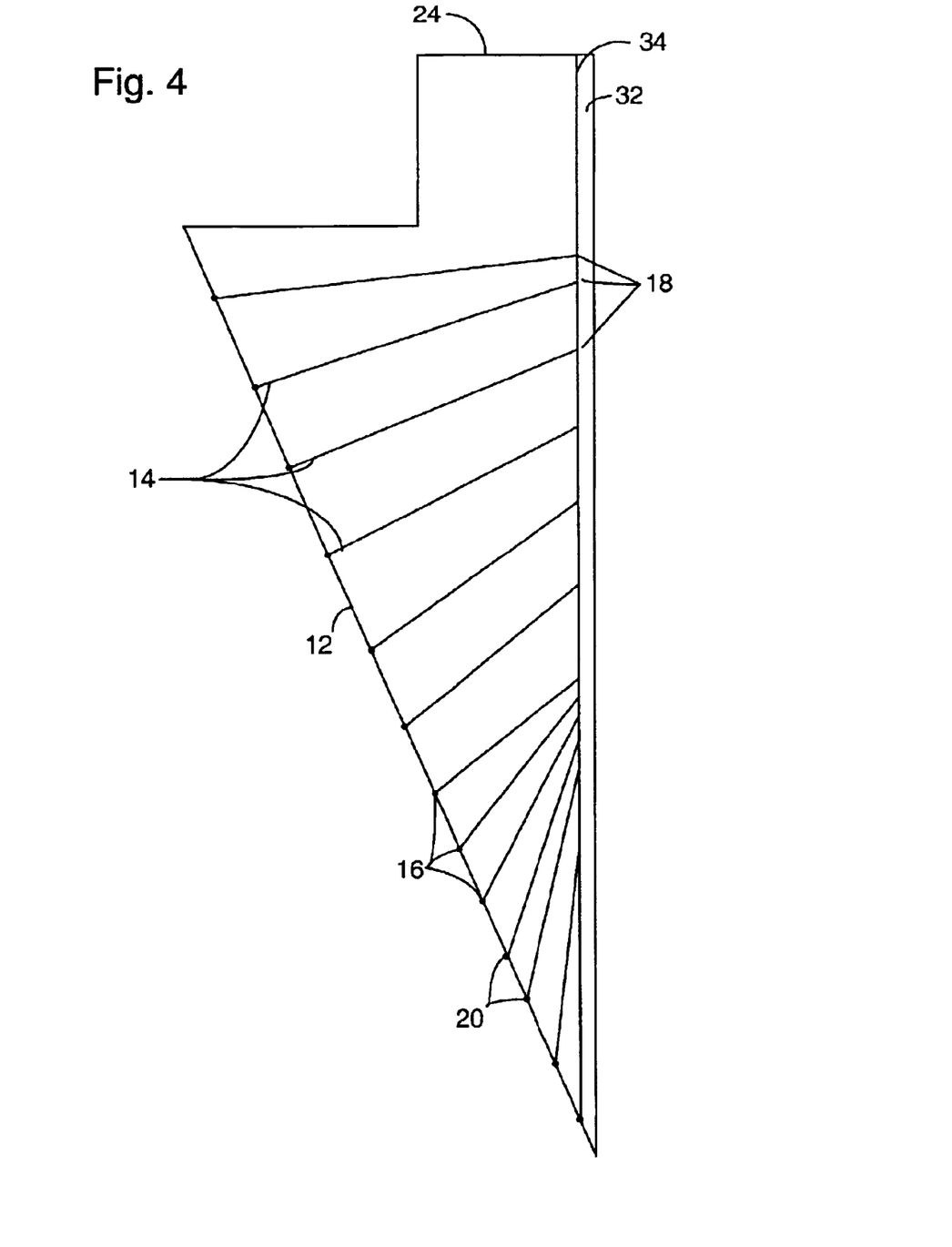
FIG. 4 is an alternate embodiment of the present invention.

An alternate embodiment of the present invention is shown in FIG. 4. The invention comprises a blade 10 having a cutting edge 12 with capillary channels 14 formed therein. The channels 14 each have an inlet end 18 and an outlet end 20. The blade 10 includes a catalyst 16 disposed near the outlet ends 20 of the channels 14. The blade 10 further includes a main channel 32 formed therein. The main channel 32 has an inlet end 34 disposed at an edge 24 distal to the cutting edge 12. The main channel 32 is in fluid communication with the inlet ends 18 of the channels 14. This provides for a larger main channel 32 and facilitates connection to a conduit, or other means, carrying a reactive gas mixture to the blade 10. Optionally, the main channel 32 decreases in diameter as the main channel 32 intersects with the channels 14 leading to the cutting edge 12.

Figure 5:
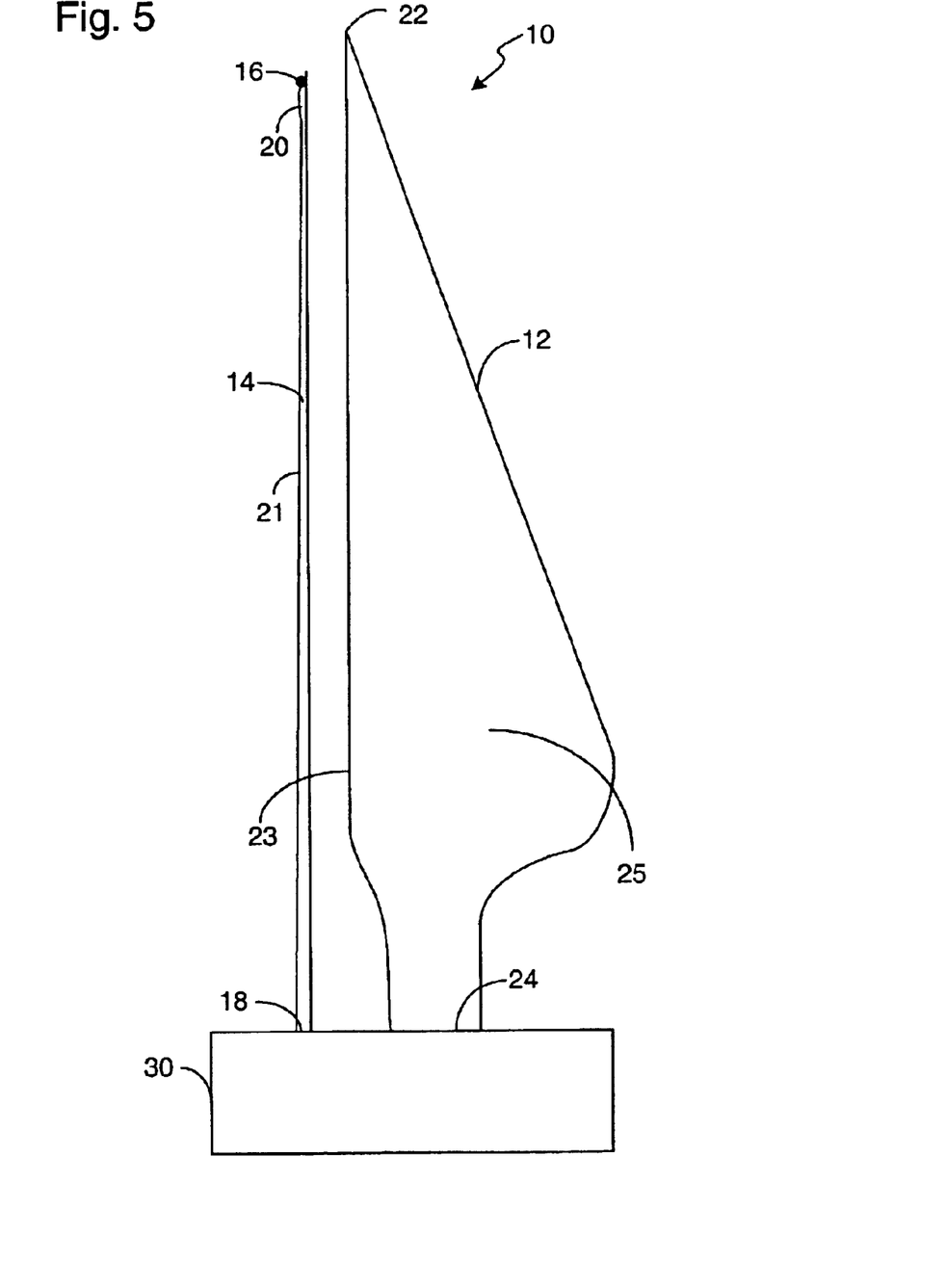
FIG. 5 is an embodiment of the present invention with a conduit and blade as separate components.

The invention is intended to cover all variations and permutations involving a blade with a conduit and a catalyst disposed proximate the end of the conduit. To that extent, an alternate embodiment includes the combination of at least one conduit 21 and a blade 10, providing an inexpensive method of producing the invention. The conduit 21 and blade 10 are held in a common handle 30 to maintain the conduit 21 in a defined relationship with respect to the blade 10, as shown in FIG. 5. This provides for an inexpensive disposable conduit 21 and blade 10, while maintaining a reusable handle 30. While not limiting the handle configuration, or design, in a preferred embodiment, the handle 30 is sized to hold a mixer (not shown), an electrolyzer (not shown), and a battery (not shown) for power to the electrolyzer. The blade 10 has a cutting edge 12, a non-cutting edge 23, and a blade surface 25. The invention includes a conduit 21 that defines a channel 14 for the transport of a mixture of reactants. The conduit 21 is positioned along the noncutting edge 23, and has an inlet end 18 and an outlet end 20 with the outlet end 20 positioned proximate to the tip 22 of the blade 10. The invention further comprises a catalyst 16 disposed proximate to the outlet end 20 of the conduit 21. In the invention's simplest form, the invention is a needle positioned next to a scalpel blade with a catalyst disposed proximate to the outlet end of the needle, wherein the needle and scalpel blade are held by a handle and in a defined relationship with respect to each other. The defined relationship can be a single fixed position, or a series of positions wherein the conduit 21, or needle, is adjustable to a desired position. Alternate embodiments include affixing the conduit 21 to the blade 10, and further includes the possibility of affixing a plurality of conduits 21 to the blade surface 25 such that the conduits 21 lie on the blade surface 25 and have outlet ends 20 positioned in a desired relationship to the cutting edge 12. The conduits 21 can be affixed to the blade 10 by any appropriate means, including but not limited to, for example welding, soldering, or use of an adhesive such as an epoxy.

Figure 6:
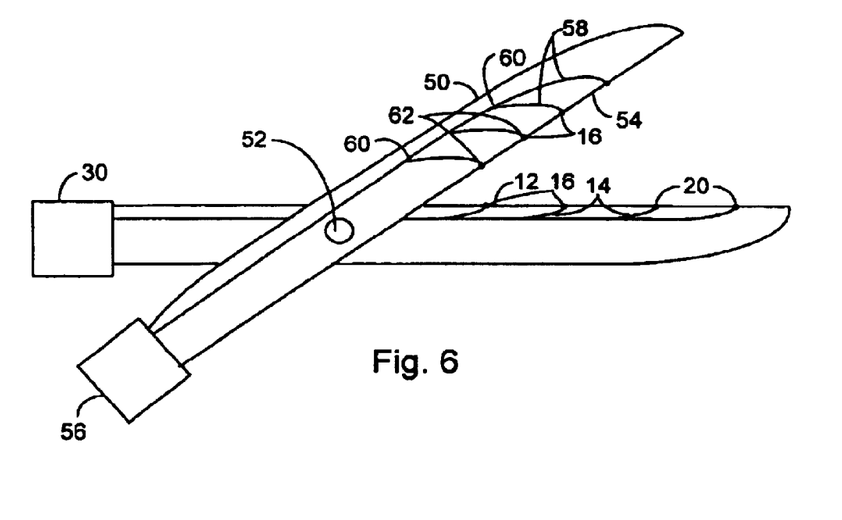
FIG. 6 is an embodiment of the invention with two blades, forming a scissors.

In another embodiment of the present invention, the invention includes a second blade 50. The blade 10 is pivotally attached to the second blade 50 by an attachment means 52 forming a scissors, as shown in FIG. 6. The second blade 50 includes at least two edges with one of the edges being a cutting edge 54. The attachment means 52 permits the blades 10, 50 to rotate about the attachment means 52 such that the cutting action is performed when one of the blade 10 and second blade 50 slides over the other. The scissors includes handles 30, 56 on each blade 10, 50 and are for moving the blades relative to each other. The blade 10 includes channels 14 formed within the blade 10, wherein each channel 14 has an inlet end 18 and an outlet end 20. The outlet ends 20 of the channels 14 are disposed proximate to the cutting edge 12 of the blade, and a catalyst 16 is disposed proximate to the outlet ends 20 of the channels. The scissors can includes a biasing means (not shown), such as for example a spring, for biasing the cutting edges 12, 54 away from each other. The blades 10, 50 are manually, or by other means, pressed toward each other such that the blades 10, 50 move past each other in a shearing motion.

Optionally, the second blade 50 is formed with a plurality of channels 58 therein. The channels 58 each have an inlet end 60 and an outlet end 62, with the outlet ends 62 disposed proximate to the cutting edge 54 of the second blade 50. A catalyst 16 is disposed proximate to the channel outlet ends 62.

Figure 6A:
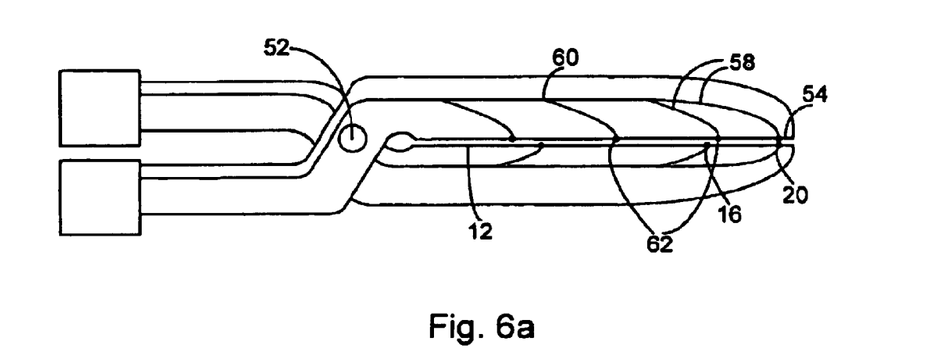
FIG. 6a is an alternate embodiment of the invention with two blades.

In another embodiment, the invention includes a second blade 50. The second blade 50 is pivotally attached to the blade 10 by an attachment means 52 to form a nipper. As described above, the second blade 50 optionally includes channels 58 formed therein. The blades 10, 50 of the nipper are manually, or by other means, pressed toward each other wherein the cutting edge 12 of the first blade 10 comes into abutting edge-to-edge contact with a complimentary edge of the second blade 50, as shown in FIG. 6a. Optionally, the complimentary edge of the second blade 50 is a cutting edge 54.

Figure 7:
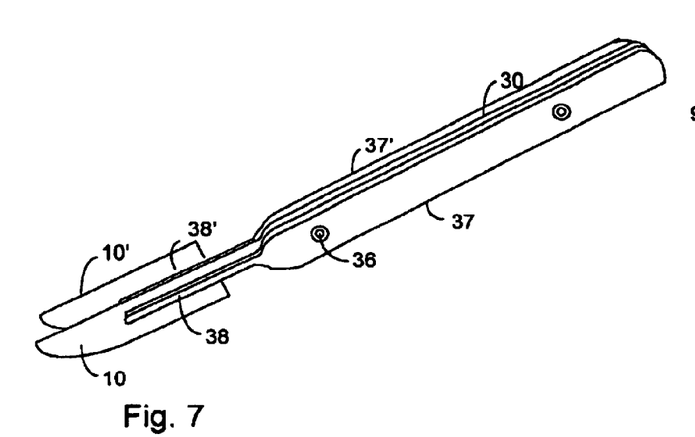
FIG. 7 is another embodiment of the invention with two blades.

In one embodiment, as shown in FIG. 7, the invention comprises at least two blades 10, 10', wherein the blades 10, 10' are parallel to each other, wherein the blades 10, 10' form a double scalpel. Each blade 10, 10' is formed as described above for a single blade, with each blade 10, 10' having channels 14 formed therein. The blades 10, 10' are releasably attached to a handle 30. The handle 30 is comprised of two members 37 and 37', each member having a corresponding connection end 38, 38' for attachment to the corresponding blade 10, 10'. The handle 30 includes an adjustment means 36 for setting the spacing between the blades 10, 10'. The adjustment means 36 may be any means for setting and holding the spacing of the two handle members 37, 37', such as for example a set screw. The handle 30 includes a conduit having at least one inlet end and at least two outlet ends. The inlet end of the conduit is in fluid communication with a source of reactant mixture, and the outlet conduit ends are in fluid communication with the channel inlet ends 18 of the blades 10, 10'.

Figure 8:
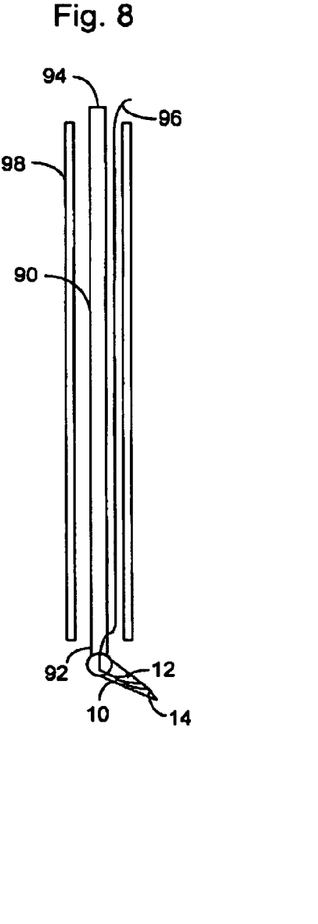
FIG. 8 is an embodiment of the invention for a remote cutting device.

The apparatus of the present invention favorably lends itself to surgical procedures involving remote surgery such as laparoscopy. In minimally invasive surgical procedures it is desired to limit the amount of bleeding, and by cauterizing capillaries during the procedure, internal bleeding can be limited. The apparatus, as shown in FIG. 8, comprises a shaft member 90 having a longitudinal axis and first 92 and second 94 ends. The apparatus is a remote cutting tool having a blade 10 is adjustably affixed to the shaft member at the first end 92 of the shaft member 90. The blade 10 includes a cutting edge 12 and has at least one capillary channel 14 formed within the blade 10. Each capillary channel 14 has an inlet end 18 and an outlet end 20, with the outlet end 20 proximate to the cutting edge 12 of the blade 10. A catalyst 16 is disposed proximate to the outlet end 20. Affixed to the second end 94 is a handle (not shown) or other means for manipulating the blade 10 affixed to the first end 92. The apparatus further includes a conduit 96 in fluid communication with the inlet ends 18 of the channels 14. The conduit 96 provides a means for supplying a chemical mixture to the catalyst 16, thereby reacting and generating heat at the cutting edge 12. Optionally, the conduit 96 is disposed within the shaft member 90. By forming the shaft member 90 with the conduit 96 within the shaft member 90, fluid communication between the inlet ends 18 of the capillary channels 14 and the source of a chemical reaction mixture is merged into a unitary piece. The blade 10 can be rotated about the longitudinal axis through rotation of the shaft member 90 by rotating the handle. The blade 10 can be pivotally attached to the shaft member 90. Pivoting the blade 10 can be performed by a spring and cable means, a second shaft member attached to the blade, or other equivalent mechanical or electro-mechanical means. Remote manipulation means are well known in the art, as shown in U.S. Pat. No. 6,051,005, which is incorporated by reference.

The remote cutting tool may optionally include a tube 98, often referred to as a cannula, through which the blade 10 and shaft member 90 are fed. The tube 98 is sized to permit access of remote operational instruments such as a laparoscope for observation of the procedure in addition to the remote cutting tool. A nominal diameter of the tube is about 1 cm.

In another embodiment of the remote cutting tool, the apparatus includes a second blade (not shown). The second blade is pivotally attached to the blade 10 and rotates about the attachment means relative to the blade 10 forming a scissors. The second blade has a cutting edge such that when the second blade pivots relative to the blade 10, the second blade slides across the cutting edge 12 of the blade 10 in a scissor-like motion. Alternately, the second blade is pivotally attached to the blade 10, and forms a nipper as described above.

The shape and design of the cutting tools is not confined to a shape for performing a straight cut, or to a blade having a substantially planar formation. In some surgical procedures, as in for example transurethral resection of the prostate, an electrocautery probe is used. The electrocautery probe is a cutting loop and the procedure is accomplished by applying a highly damped radio frequency current to the tissue through the probe. To achieve adequate performance the probe must be moved very slowly which increases operative time. Since operative time is limited by the safe time that a patient can withstand anesthesia, trauma, etc., the slow performance limits the amount of area of tissue that can be treated. The use of a shaped cutting blade that is heated through chemical reactions can provide a faster response and allow for a greater amount of tissue to be treated.

Figure 9:
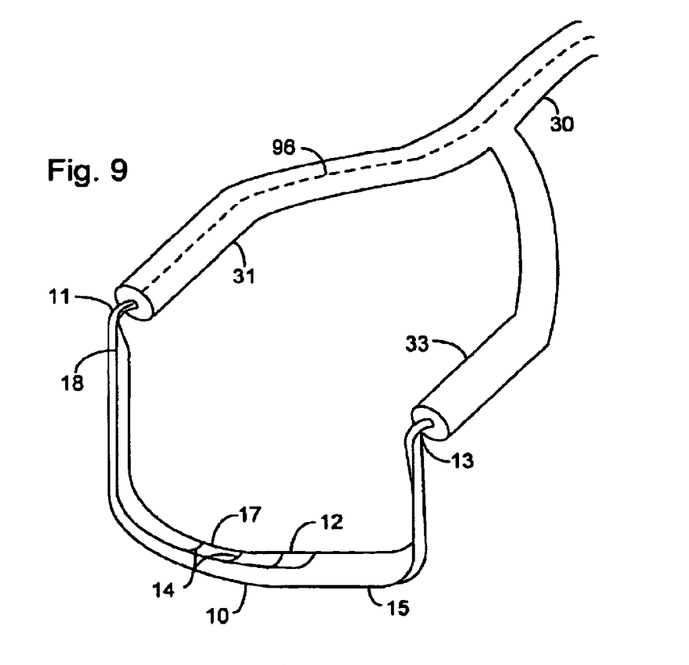
FIG. 9 is an embodiment of the invention with a blade shaped for scraping tissue.

The shaped cutting tool as shown in FIG. 9 comprises a blade 10 having a first end 11 and a second end 13 opposite the first end 11. The blade 10 has at least one cutting edge 12 located between the first 11 and second 13 ends, with a leading edge 15 and a trailing edge 17. The blade 10 is affixed to a handle 30 having a pair of arms 31, 33, wherein the first end 11 is attached to one of the pair of arms 31, 33 and the second end 13 is attached to the other of the pair of arms 31, 33. The blade 10 is formed with a plurality of channels 14 defined therein. The channels 14 each have an inlet end 18 and an outlet end 20. The outlet end 20 of each channel 14 is located proximate to the cutting edge 12 of the blade 10. The blade 10 includes a catalyst 16 located proximate to the outlet ends 20 of the channels. The blade 10 may be formed using the methods described above, such as using two thin plates, wherein the channels 14 are formed in one plate, and bonding the second plate over the channels 14. The blade 10 may be sharpened, and then formed into a desired configuration. One such configuration, as shown in FIG. 9, has a general U-shape. As an alternative, the plates are formed into the desired shape, the channels 14 are formed in one plate, and then the second plate is bonded with the first plate.

The channel inlet ends 18 are located at either the first end 11 or second end 13 of the blade. Depending on the number and distribution of channels 14 within the blade 10, the inlet ends may be distributed between the first end 11 and the second end 13. A conduit 96 is in fluid communication with the inlet ends 18 of the channels 14 for supplying a chemical mixture to the channels 14. The conduit 96 may optionally be a channel formed within the handle 30 that runs through the handle arms 31, 33 to connect with the channel inlet ends 18.

While the blade 10 in FIG. 9 is depicted as substantially perpendicular to the handle 30, the orientation of the blade 10 is not limited to this configuration. On the contrary, the orientation of the blade 10 relative to the handle 30 can be any angle from substantially parallel to substantially perpendicular to the handle 30. The cutting edge 12 maybe located on a leading edge 15 of the blade 10, a trailing edge 17 of the blade 10, or both the leading 15 and trailing 17 edges of the blade 10.

Figure 10:
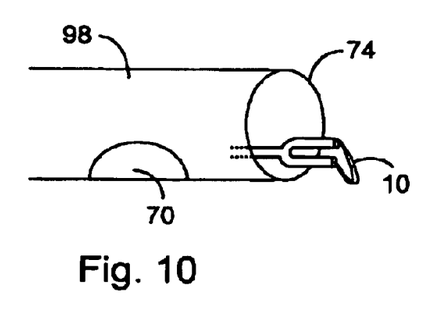
FIG. 10 is an embodiment of the invention with a blade for cutting over an aperture.

An embodiment of the shaped cutting tool includes a tube 98 sized to permit movement of the blade 10 is shown in FIG. 10. The tube 98 has a leading end 74 to be positioned near tissue to be cut. The tube 98 includes an aperture 70 within a wall of the tube proximate to the leading edge. The leading end 74 of the tube 98 can be open, or closed with a rounded end to permit smooth insertion of the tube 98. The aperture 70 permits access of tissue to be cut by the blade 10. The blade 10 is shaped to conform with the shape of the interior surface of the tube 98. The blade 10 slides in a longitudinal direction over the aperture 70 to cut tissue projecting into the tube 98 through the aperture 70. The blade 10 can also have a straight configuration, wherein the blade 10 slides over the aperture through rotation of the handle 30 within the tube 98.

Figure 11:
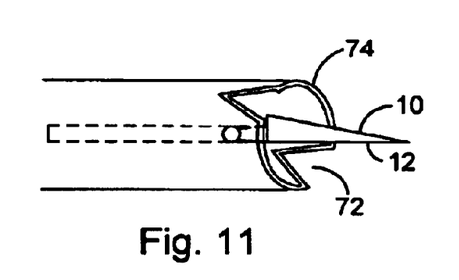
FIG. 11 is an embodiment of the invention with a blade for cutting over a notch.

An alternate design includes at least one notch 72 in an open leading end 74 of the tube 98, as shown in FIG. 11. The blade 10 slides over the notch 72 cutting tissue positioned within the notch 72. The blade 10 is of a design having a straight cutting edge 12, and slides over the notch 72 through rotation of the cutting tool within the tube 98. Alternately, the blade 10 is designed to conform to the shape of the interior wall of the tube 98 and slides over the notch in a longitudinal direction.

Figure 12:
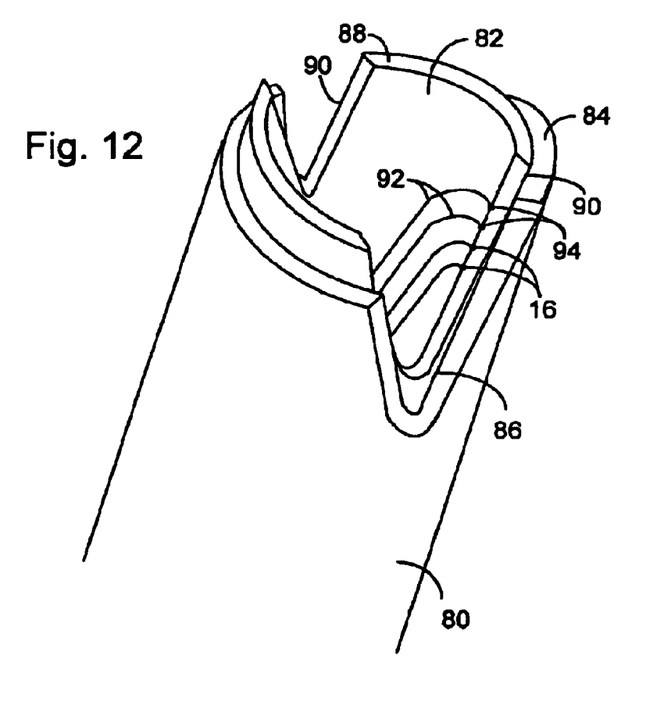
FIG. 12 is an embodiment of a cutting tool having an inner tubular member and an outer tubular member.

The cutting tool is not confined to a blade, but may be any cutting tool used in surgical procedures. A cutting tool can take the form of an arthroscopic cutting tool, as shown in FIG. 12. The cutting tool comprises an outer tubular member 80 and an inner member 82. The outer tubular member 80 has a longitudinal axis, a first end 84 and a second end opposite the first end, wherein the first end 84 is inserted into a patient for cutting tissue. The first end 84 includes at least one notch 86, wherein tissue to be cut is positioned. The inner tubular member 82 has a longitudinal axis, a first end 88 and a second end opposite the first end 88. The first end 88 of the inner tubular member 82 includes a sharpened edge 90 for cutting proximate to the first end 88. The inner tubular member 82 is sized such that the outer surface of the inner tubular member 82 is in contact with the inner surface of the outer tubular member 80. The inner tubular member 82 can move along the longitudinal axis within the outer tubular member 80, or can rotate around the longitudinal axis within the outer tubular member 80. The sharpened edge 90 of the inner tubular member 82 slides over the inner surface of the outer tubular member 80 when the inner tubular member 82 is rotated around the longitudinal axis relative to the outer tubular member 80.

The inner tubular member 82 has in interior surface and includes capillaries 92 affixed to the interior surface. The capillaries 92 have inlet ends and outlet ends 94, wherein the outlet ends 94 are positioned proximate to the sharpened edge 90. A catalyst 16 is disposed on the inner tubular member 82 proximate to the sharpened edge 90. In one embodiment, capillaries 92 are formed of a flexible material that is impermeable to hydrogen and oxygen. The capillaries 92 are positioned on the interior surface of the inner tubular member 82 with the outlet ends 94 positioned near the sharpened edge 90. The capillaries 92 are bonded to the inner surface of the inner tubular member 82 with an appropriate bonding agent, for example an epoxy resin. The inlet ends of the capillaries 92 extend to at least the second end of the inner tubular member 82 where the inlet ends 94 of the capillaries 92 are in fluid communication with a source of a gaseous mixture of hydrogen and oxygen. Preferably, the source of hydrogen and oxygen are generated from an electrolyzer as described above. The hydrogen and oxygen from the electrolyzer are directed to inlet ports of a mixing chamber and mixed in the chamber producing a mixture. The mixture is directed to an outlet port of the mixing chamber in fluid communication with the inlet ends of the capillaries.

In an alternate embodiment, the inner tubular member 82 moves in a longitudinal direction relative to the outer tubular member 80 and the sharpened edge 90 slides over the notch 86 cutting through tissue positioned within the notch 86. There are many other obvious variations on the cutting tool, including for example an embodiment (not shown) with an aperture in the side of the outer tubular member and proximate to the first end, all of which are contemplated by the present invention.

Additional cutting tools include the leading edge of a dissector which can be adapted to be covered by the present invention for surgery where bleeding is expected and cauterization of capillaries is desired. Although the dissector is relatively blunt when compared with a scalpel blade, the dissector is sometimes used to separate tissue and in the separation process bleeding can occur. The cutting edge of a resector is also contemplated to be covered by this invention.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. An apparatus for cutting comprising:
    a blade comprising a cutting edge and defining at least one primary channel, each primary channel having an inlet end and outlet end with the outlet end proximate to the cutting edge; and
    a catalyst disposed proximate to the outlet end of each primary channel.

2. The apparatus of claim 1 wherein the catalyst is disposed within each primary channel proximate to the primary channel outlet end.

3. The apparatus of claim 1 wherein each primary channel has a diameter of less than 400 micrometers.

4. The apparatus of claim 3 wherein each primary channel has a diameter of less than 200 micrometers.

5. The apparatus of claim 4 wherein each primary channel has a diameter of less than 100 micrometers.

6. The apparatus of claim 1 wherein the blade further comprises an edge distal to the cutting edge and defining the inlet end of at least one primary channel.

7. The apparatus of claim 6 further comprising a blade holder affixed to the end of the blade proximate to the distal edge.

8. The apparatus of claim 6 further comprising a mixer, comprising:
    at least one first supply tube having a first supply tube receiving end for receiving a first fluid stream and having a first supply tube discharge end opposite the first supply tube receiving end;
    at least one second supply tube having a second supply tube receiving end for receiving a second fluid stream and having a second supply tube discharge end opposite the second supply tube receiving end;
    a mixing chamber in fluid communication with the first and second supply tube discharge ends; and
    a mixing chamber outlet for discharging a mixed stream of the first and second fluid streams from the mixing chamber, the mixing chamber outlet in fluid communication with the central region of the mixing chamber, and the mixing chamber outlet in fluid communication with the inlet end of each primary channel.

9. The apparatus of claim 8 wherein one of the first or second supply tube discharge ends leads substantially tangentially into the mixing chamber and the other of the first and second supply tube discharge ends leads substantially radially into the mixing chamber.

10. The apparatus of claim 8 wherein the mixing chamber further includes a packed porous bed.

11. The apparatus of claim 8 wherein the mixing chamber includes a static mixer for providing a mixture of the first and second fluid streams and having a dimension less than a dimension necessary to initiate a reaction of the mixture.

12. The apparatus of claim 8 further comprising an electrolyzer having means for electrical power, an inlet port, an oxygen outlet port, and a hydrogen outlet port, wherein the oxygen outlet port is in fluid communication with the first or second supply tube receiving end and the hydrogen outlet port is in fluid communication with the other of the first or second supply tube receiving ends.

13. The apparatus of claim 12 wherein the electrolyzer is sized to dissociate water at a rate between about 0.01 milligrams/minute and about 10 grams/minute.

14. The apparatus of claim 12 further comprising a control system for controlling the rate of supply of reactants to the inlet ends of the primary channels.

15. The apparatus of claim 14 wherein the control system controls the electrical power delivered to the electrolyzer.

16. The apparatus of claim 6 further comprising an electrolyzer having an inlet port, an oxygen outlet port and a hydrogen outlet port, wherein the oxygen and hydrogen outlet ports are each in fluid communication with the inlet end of the plurality of primary channels.

17. The apparatus of claim 1 the blade further comprising an edge distal to the cutting edge defining a main channel having an inlet end and at least one outlet end, wherein the main channel outlet end is in fluid communication with the inlet end of each primary channel and the main channel inlet end is proximate to the distal edge.

18. The apparatus of claim 1 wherein the blade is made of a material selected from the group consisting of stainless steels, ceramics, glasses, quartz, thermoset plastics, and alloys of metals.

19. The apparatus of claim 18 wherein the blade is made of stainless steel.

20. The apparatus of claim 1 wherein the catalyst is a material selected from the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Ti), tin (Sn), lead (Pb), antimony (Sb), bismuth (Bi), polonium (Po), and mixtures thereof.

21. The apparatus of claim 20 wherein the catalyst is a material selected from the group consisting of platinum, palladium, rhenium, rhodium, nickel, iron, ruthenium, and mixtures thereof.

22. The apparatus of claim 1 wherein each of the primary channels is a pair of secondary channels, and wherein one of each pair of secondary channels carries a first reactant, and the other of each pair of secondary channels carries a second reactant, and wherein the outlets of each pair of secondary channels are in proximity to each other.

23. The apparatus of claim 1 further comprising:
a second blade having at least two edges and defining at least one channel formed therein, wherein at least one edge is a cutting edge and wherein each channel has an inlet end and outlet end with the outlet end proximate to the cutting edge, and wherein the second blade is interconnected to the first blade and having a substantially parallel separation from the first blade; and
a catalyst disposed proximate to the outlet end of each channel 24. The apparatus of claim 1 further comprising:
a second blade having at least two edges and pivotally connected to the first blade, wherein the cutting edge of the first blade comes into abutting edge-to-edge contact with a complimentary edge of the second blade.

25. The apparatus of claim 24 wherein the second blade comprises a cutting edge disposed on the complimentary edge of the second blade.

26. The apparatus of claim 1 further comprising:
a second blade having at least two edges and pivotally connected to the first blade, wherein the cutting edge of the first blade is allowed to slide across one of the edges of the second blade in a shearing motion.

27. The apparatus of claim 26 wherein the second blade defines at least one channel formed therein and has a cutting edge, and wherein the channel has an inlet end and an outlet end with the outlet end proximate to the cutting edge; and
a catalyst disposed proximate to the second blade cutting edge.

28. A cauterizing scalpel to simultaneously incise and cauterize tissue comprising:
a blade holder;
a blade having at least one cutting edge, an edge distal to the cutting edge for connection to the blade holder for holding the blade;
a conduit having an inlet end and an outlet end, wherein the inlet end is connected to the blade holder, and the conduit is held in a defined position relative to the blade; and
a catalyst disposed proximate to the outlet end of the conduit.

29. The scalpel of claim 28 wherein the conduit is a needle forming a channel with a channel diameter of less than 400 micrometers.

30. The scalpel of claim 28 wherein the catalyst is a material selected from the group consisting of scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), germanium (Ge), indium (In), thallium (Ti), tin (Sn), lead (Pb), antimony (Sb), bismuth (Bi), polonium (Po), and mixtures thereof.

31. The scalpel of claim 30 wherein the catalyst is a material selected from the group consisting of platinum, palladium, rhenium, rhodium, nickel, iron, ruthenium, and mixtures thereof.

32. The scalpel of claim 28 wherein the conduit is affixed to the blade.

33. The scalpel of claim 32 wherein the conduit is defined by channels formed within the blade.

34. The scalpel of claim 28 further comprising a mixer disposed within the blade holder.

35. The scalpel of claim 28 further comprising an electrolyzer disposed within the blade holder.

36. The scalpel of claim 35 further comprising an electric power source disposed within the blade holder for providing electric power to the electrolyzer.

37. An apparatus for remote cutting comprising:
a shaft member having a longitudinal axis and first and second ends;
a blade operably affixed to the first end of the shaft member, having at least one cutting edge and defining at least one channel formed therein, wherein the channel has an inlet end and an outlet end with the outlet end proximate to the cutting edge;
a catalyst disposed proximate to the channel outlet end; and
a conduit in fluid communication with the channel inlet end in the blade.

38. The apparatus of claim 37 wherein the conduit is defined by a channel disposed within the shaft member.

39. The apparatus of claim 38 further comprising:
an outer cylindrical conduit defining an inner cylindrical surface and having a longitudinal axis, an open first end, an open second end, and at least one notch disposed in the open second end;
wherein the shaft member is adapted to move within the outer cylindrical conduit, and wherein the blade is arcuated and adjacent to the inner cylindrical surface, and wherein the cutting edge is positioned to slide over the notch.

40. The apparatus of claim 38 further comprising:
an outer cylindrical conduit having a longitudinal axis, an inner cylindrical surface, an open first end, an open second end, and at least one notch disposed in the open second end;
wherein the shaft forms an inner cylindrical member and is adapted to rotate within the outer cylindrical conduit, and wherein the blade is adjacent to the inner cylindrical surface, and wherein the cutting edge is positioned to slide over the notch.

41. The apparatus of claim 40 wherein the blade is defined by a notch in the inner cylindrical member.

42. The apparatus of claim 37 wherein the catalyst is a material selected from the group consisting of platinum, palladium, rhenium, rhodium, nickel, iron, and mixtures thereof.

43. The apparatus of claim 37 wherein each channel has a diameter of less than 200 micrometers.

44. The apparatus of claim 37 wherein the blade is pivotally adjustable relative to the longitudinal axis of the shaft member.

45. The apparatus of claim 37 further comprising a second blade pivotally affixed to the blade, wherein the second blade comprises a cutting edge such that the blade and second blade form a scissors.

46. The apparatus of claim 37 further comprising a mixer, comprising:
at least one first supply tube having a first supply tube receiving end for receiving a first fluid stream and having a first supply tube discharge end opposite the first supply tube receiving end;
at least one second supply tube having a second supply tube receiving end for receiving a second fluid stream and having a second supply tube discharge end opposite the second supply tube receiving end;
a mixing chamber in fluid communication with the first and second supply tube discharge ends; and
a mixing chamber outlet for discharging a mixed stream of the first and second fluid streams from the mixing chamber, the mixing chamber outlet in fluid communication with the central region of the mixing chamber, and the mixing chamber outlet in fluid communication with the inlet end of the channels.

47. The apparatus of claim 37 further comprising an electrolyzer having an inlet port, an oxygen outlet port and a hydrogen outlet port, wherein the oxygen outlet port and the hydrogen outlet port are in fluid communication with the inlet end of the channels.

48. The apparatus of claim 37 further comprising:
a cannula having a longitudinal axis, an inner surface, an open first end, and an aperture disposed near the end opposite the first end, wherein the shaft member can move within the cannula and wherein the blade is adjacent to the inner surface of the cannula and adapted to move within the cannula and slide over the aperture.

49. An apparatus for remote cutting comprising:
an outer cylindrical conduit defining an inner cylindrical surface and having a longitudinal axis, an open first end, an open second end, and at least one notch disposed in the open first end;
a shaft member having a longitudinal axis and first and second ends, wherein the shaft member is adapted to move within the outer cylindrical conduit;
a blade operably affixed to the first end of the shaft member having at least one cutting edge wherein the cutting edge is positioned to slide over the notch;
a gas conduit defining a channel for carrying a gas mixture, and having an inlet end and an outlet end wherein the outlet end is proximate to the notch of the outer conduit; and
a catalyst disposed proximate to the outlet end of the gas conduit.

50. The apparatus of claim 49 wherein the shaft member forms an inner cylindrical member and is adapted to rotate within the outer cylindrical conduit, and wherein the blade is defined by a notch in the inner cylindrical member.

51. A cutting apparatus comprising:
a blade having a first end and a second end opposite the first end and a cutting edge disposed therebetween, and defining at least one channel formed therein wherein each channel has an inlet end and outlet end with the outlet end proximate to the cutting edge and the inlet end proximate to one of the first or second ends;
a pair of arms affixed to the first and second ends of the blade; and
a catalyst disposed proximate to the outlet end.

52. The apparatus of claim 51 wherein the blade is a cutting loop for a cautery probe, and wherein the blade forms a loop having a substantially U-shape.

* * * * *